(12) United States Patent
Saigoku et al.

(10) Patent No.: US 8,357,820 B2
(45) Date of Patent: Jan. 22, 2013

(54) PROCESS FOR PRODUCING N-PROTECTED AMINO ACID

(75) Inventors: Tomoaki Saigoku, Hachimantai (JP); Takaharu Iwaki, Matsusaka (JP); Masato Sakuyama, Hachimantai (JP)

(73) Assignee: Sekisui Medical Co., Ltd., Tokyo (JP)

( * ) Notice: Subject to any disclaimer, the term of this patent is extended or adjusted under 35 U.S.C. 154(b) by 355 days.

(21) Appl. No.: 12/883,300

(22) Filed: Sep. 16, 2010

(65) Prior Publication Data

US 2011/0152573 A1     Jun. 23, 2011

Related U.S. Application Data

(60) Provisional application No. 61/243,205, filed on Sep. 17, 2009.

(51) Int. Cl.
*C07C 269/04* (2006.01)
*C07C 271/22* (2006.01)
*C07B 51/00* (2006.01)
*C07B 53/00* (2006.01)

(52) U.S. Cl. ......... 562/507; 562/553; 562/554; 562/575

(58) Field of Classification Search .................. None
See application file for complete search history.

(56) References Cited

OTHER PUBLICATIONS

Doyle et al. Journal of the Chemical Society, 1962, 1440-4.*

* cited by examiner

*Primary Examiner* — Yevegeny Valenrod
(74) *Attorney, Agent, or Firm* — Birch, Stewart, Kolasch & Birch, LLP

(57) ABSTRACT

The present invention relates to a method for producing N-protected amino acid. Specifically, the present invention provides a method in which a protecting group is introduced to the amino group of an amino acid in a reaction under alkaline condition, and the N-protected amino acid thus generated is then separated from the reaction solution as crystals, without undergoing an extraction step or a concentration step. The present inventors have completed the invention based on the finding that desirable crystals of N-protected amino acids may be obtained without extraction, concentration or recrystallization steps between the initial generation of the N-protected amino acid molecules and the subsequent separation of the crystals, by first adding an water-soluble organic solvent and optionally water to the reaction solution (alkaline) containing the N-protected amino acid, and then neutralizing the solution by an acid.

7 Claims, No Drawings

US 8,357,820 B2

PROCESS FOR PRODUCING N-PROTECTED AMINO ACID

CROSS-REFERENCE TO RELATED APPLICATION

This application is entitled to the benefit of, as well as claims priority to, U.S. Provisional Patent Application Ser. No. 61/243,205, filed Sep. 17, 2009 under the title "A Method for Producing N-Protected Amino Acid", the contents of which are incorporated herein by reference in their entirety.

FIELD OF THE INVENTION

The present invention relates to a method for producing N-protected amino acid. Specifically, the present invention provides a method in which a protecting group is introduced to the amino group of an amino acid in a reaction under alkaline condition, and the N-protected amino acid thus generated is then separated as crystals from the reaction solution, without undergoing an extraction step or a concentration step.

BACKGROUND OF THE INVENTION

N-Protected amino acids, in which the amino groups are protected by protecting groups such as carbobenzyloxy group (hereafter referred to as Cbz group) are commonly used as materials for peptide synthesis. Among the N-protected amino acids, N-carbobenzyloxy-L-cyclohexylglycine (hereafter referred to as Cbz-CHG) is an important intermediate for certain medical drugs that contain peptide structures within their molecules, such as anti-virus drugs having serine-protease inhibitor activity and anti-arthritis drugs having metalloproteinase inhibitor activity.

A known method of producing an N-protected amino acid, Cbz-glycine in the present example, is as follows: glycine is reacted with carbobenzyloxy chloride (hereafter referred to as Cbz-Cl) under an alkaline condition (NaOH) to generate Cbz-glycine, the reaction solution is washed with a poor solvent (ether), and the crystals are then allowed to form under a cold and acidic (hydrochloric acid) condition, isolated by filtration, and recrystallized from chloroform to give Cbz-glycine (Non-Patent Document 1).

However, the method of Non-Patent Document 1 is not readily applicable to the production of Cbz-CHG, because when the reaction solution (in which Cbz-CHG has been generated under alkaline condition) is washed with a poor solvent and an acid is added, a gum-like mass instead of crystal will form.

Another commonly-used method for producing a protected amino acid is as follows: after an amino acid starting material is subjected to a reaction to generate its protected form, the product is once extracted from the reaction solution with an organic solvent that does not mix with the reaction solution, and the organic solvent is then removed by evaporation and a poor solvent is added as needed to allow the reaction product to crystallize. In the production of low-melting point amino acid derivatives, this method is known to enable crystallization of the protected amino acids of interest even from the oily materials, by the use of multiple organic solvents, a cooled organic solvent, or other variations.

The present inventors have tested the above method (hereafter also referred to as the conventional extraction/crystallization method) on Cbz-CHG, by performing organic solvent extraction of the reaction solution in which Cbz-CHG was generated under alkaline condition, and have been able to obtain Cbz-CHG crystals successfully. However, this method involves many steps such as extraction step and concentration step and therefore suffers from high cost. Another problem associated with this method is that it requires the use of large quantity of organic solvents that may be hazardous due to, for example, their toxicity or flammability.

References Cited

Non-Patent Document 1
  "The basics and the experiments of peptide synthesis", page 18 (Maruzen Co. Ltd., published Jan. 20, 1985)

SUMMARY OF THE INVENTION

Problem to Be Solved by the Invention

An object of the present invention is to provide a method for producing N-protected amino acids, especially the N-protected form of cyclohexylglycine (hereafter also referred to as CHG), more specifically N-carbobenzyloxy-L-cyclohexylglycine, that involves fewer steps and uses a smaller amount of organic solvent as well as fewer types of organic solvents compared to the conventional extraction/crystallization method.

Means of Solving the Problem

The present inventors have conducted extensive research on Cbz-CHG production processes and found that desirable crystals of Cbz-CHG may be obtained without the necessity of an extraction, concentration or recrystallization step between the initial generation of Cbz-CHG and the subsequent separation of the crystals, by first adding a water-soluble organic solvent to the Cbz-CHG-containing reaction solution (alkaline) prior to neutralizing the solution with acid, instead of directly adding the acid to the Cbz-CHG-containing reaction solution (alkaline) as in Non-Patent Document 1. This finding has led to the completion of the present invention.

In other words, the present invention has made it possible to obtain N-protected amino acid crystals from the reaction solution (in which the protecting group has been introduced to the amino group of the amino acid under alkaline condition and the N-protected amino acid has thus been generated) without performing an extraction step or a concentration step. More specifically, the present invention is as described in [1]-[7] below.

[1] A method for producing N-protected amino acid comprising:
 (1) a step of introducing a protecting group to an amino group of an amino acid under an alkaline condition and thus generating an N-protected amino acid,
 (2) a step of adding a water-soluble organic solvent, and optionally water, to the above reaction solution, and
 (3) a step of neutralizing or acidifying the reaction solution following step (2) and obtaining the N-protected amino acid in the crystal form.
[2] The method according to [1], wherein the amino acid is L-cyclohexylglycine.
[3] The method according to [1] or [2], wherein the N-protected amino acid is N-carbobenzyloxy-L-cyclohexylglycine.
[4] The method according to any of [1] to [3], wherein the water-soluble organic solvent is isopropyl alcohol.
[5] The method according to any of [1] to [4], wherein 0 to 0.98 volumes of water and 0.14 to 0.56 volumes of isopropyl alcohol are added in step (2) relative to the reaction volume of step (1) in which the N-protected amino acid has been generated.

[6] The method according to any of [1] to [4], wherein 0.01 to 0.98 volumes of water and 0.14 to 0.56 volumes of isopropyl alcohol are added in step (2) relative to the reaction volume of step (1) in which the N-protected amino acid has been generated.

[7] The method according to any of [1] to [4], wherein 0.49 to 0.75 volumes of water and 0.27 volumes of isopropyl alcohol are added in step (2) relative to the reaction volume of step (1) in which the N-protected amino acid has been generated.

EFFECTS OF THE INVENTION

According to the present invention, a method is provided for production of N-protected amino acids, especially the N-protected form of cyclohexylglycine, more specifically N-carbobenzyloxy-L-cyclohexylglycine, wherein the method involves fewer steps and uses a smaller amount of organic solvent as well as fewer types of organic solvents compared to the conventional extraction/crystallization method. According to the present invention, it is possible to obtain crystals of N-protected amino acid from the alkaline reaction solution in which the protecting group has been introduced to the amino group of the amino acid and the N-protected amino acid has thus been generated, without the necessity of an extraction step or a concentration step.

Mode for Carrying Out the Invention

Examples of "amino acids" to which the method of the present invention may be applied include glycine, alanine, and cyclohexylglycine. Cyclohexylglycine is preferred among these examples.

The "alkaline condition" under which the N-protected amino acid is generated in step (1) of the present invention refers to a condition in which the amino group to be protected attains sufficient nucleophilicity. This "alkaline condition" may be obtained, for example, by the use of NaOH in a manner well known to a person skilled in the art.

Examples of "protecting groups" in the present invention include carbobenzyloxy group (this group is herein denoted as 'Cbz-'. However, it is identical to the group denoted as 'Z-'). A compound that can provide a protection to amino groups under the said alkaline condition is preferred as a reagent for introducing the protecting group. A specific example of this is Cbz-Cl.

The "step of introducing a protecting group to an amino group of an amino acid under an alkaline condition and thus generating an N-protected amino acid" in the present invention may be modified as needed according to the above descriptions.

The water-soluble organic solvent used in the "step of adding a water-soluble organic solvent, and optionally water, to the above reaction solution" in the present invention may be an organic solvent that shows mutual solubility with water and mixes readily with water (hereafter referred to as water-soluble organic solvent). Ethanol or isopropyl alcohol may be used favorably, but isopropyl alcohol is especially preferred.

In the "step of neutralizing or acidifying the reaction solution following step (2) and obtaining the N-protected amino acid in the crystal form" of the present invention, the acid for neutralizing or acidifying the said reaction solution, to which the water-soluble organic solvent and optionally water have been added, may be any acid known to a person skilled in the art, as long as it does not interfere with the generation and crystallization of Cbz-L-CHG; hydrochloric acid is especially preferred.

The crystals, formed after the addition of water-soluble organic solvent (isopropyl alcohol) and optionally water to the reaction solution and the subsequent neutralization of the reaction solution by the addition of acid (hydrochloric acid), may be isolated by filtration and dried to present the N-protected amino acid (Cbz-L-CHG).

Subsequent to the method of the present invention described above, if needed, further purification steps such as recrystallization may be performed.

In step (2) of the above-mentioned method [1], the optimal ranges of the amounts of the water-soluble organic solvent and the optionally added water may each be experimentally established as in the manner described in the Example, based on the amount of the N-protected amino acid (Cbz-CHG) generated and/or the volume of the reaction solution in step (1).

If the water-soluble organic solvent used therein is isopropyl alcohol, it is favorable to add 0 to 1.00 volume of water, preferably 0 to 0.98 volumes of water, and 0.10 to 0.60 volumes of isopropyl alcohol, preferably 0.14 to 0.56 volumes of isopropyl alcohol, to the reaction solution of step (1) in which the N-protected amino acid has been generated. It is more preferable to add 0.49 to 0.75 volumes of water and 0.27 volumes of isopropyl alcohol.

The volume of the reaction solution of step (1) may be determined by actual measurement. Alternatively, it may be conveniently estimated based on the total volume of the solvent added in step (1), or based on the total amounts of the solutes and the solvent (assuming 1 kg=1 L) added in step (1).

The method of the present invention which comprises the optional addition of water and the subsequent addition of the water-soluble organic solvent to the reaction solution, followed by neutralization thereof by the acid, not only reduces the number of steps, the amount of organic solvent used, and the number of types of organic solvents used compared to the conventional extraction/crystallization method, but also enables the entire series of manipulations to be performed in the same reaction vessel, which represents a stark contrast to the conventional extraction/crystallization method where multiple vessels are required for accommodating the different manipulations (extraction, then concentration, etc.).

EXAMPLES

The present invention is illustrated in further detail in the following Examples, but the present invention is by no means limited by these Examples.

Comparative Example 1

2460 L of water and 250 L of 20% aqueous solution of NaOH were added to 246 kg of L-CHG to dissolve the L-CHG. To the above solution of L-CHG 267 kg of Cbz-Cl and 280 L of 20% aqueous solution of NaOH were added drop-wise, to introduce the Cbz group into L-CHG.

After 1930 L of ethyl acetate was added to the above reaction solution, the solution was neutralized by the addition of 170 L hydrochloric acid, and the extraction step was performed. The extract was washed with 500 L water 3 times, and then concentrated under a reduced pressure. Following the concentration step under the reduced pressure, 3200 L of n-heptane was added to the concentrated residue, and the crystals formed therein were isolated by filtration and dried; 375 kg of Cbz-L-CHG was thus obtained.

The yield was 82.3%, the chemical purity was 99.5%, and the optical purity was 100.0%.

Chemical purity was determined by the reversed phase HPLC assay, and optical purity was determined by the normal phase chiral HPLC assay. The same assays were used in the sections described below.

Example 1

Step (1): 534 mL of water and 60.9 mL of 20% aqueous solution of NaOH were added to 60.0 g of L-CHG to dissolve the L-CHG. The solution was treated with activated carbon, and 79 mL of water was added. To this solution, 65.1 g of Cbz-Cl and 60.9 mL of 20% aqueous solution of NaOH were added drop-wise, to introduce the Cbz group into L-CHG.

Step (2): The reaction solution above (volume: 865 mL) was divided into 10 equal parts, and water and isopropyl alcohol (IPA) were added to each part at the ratios indicated in Table 1.

Step (3): After step (2), 4.1 mL of hydrochloric acid was added to the reaction solution for neutralization, and the crystals formed were isolated by filtration. The filter-isolated crystals were dried and Cbz-L-CHG was thus obtained.

The result obtained in each condition is shown in Table 1.

TABLE 1

| condition | water | IPA | yield | chemical purity | optical purity |
|---|---|---|---|---|---|
| A | 0.0 mL(0.00) | 12.1 mL(0.14) | 84.8% | 99.6% | 100% |
| B | 0.0 mL(0.00) | 23.4 mL(0.27) | 88.9% | 99.6% | 100% |
| C | 0.0 mL(0.00) | 36.3 mL(0.42) | 86.7% | 99.6% | 100% |
| D | 0.0 mL(0.00) | 48.4 mL(0.56) | 86.0% | 99.5% | 100% |
| E | 21.6 mL(0.25) | 23.4 mL(0.27) | 89.0% | 99.7% | 100% |
| F | 42.4 mL(0.49) | 23.4 mL(0.27) | 90.0% | 99.7% | 100% |
| G | 64.9 mL(0.75) | 23.4 mL(0.27) | 91.9% | 99.8% | 100% |
| H | 84.8 mL(0.98) | 23.4 mL(0.27) | 88.9% | 99.5% | 100% |

*The values in parentheses represent relative volumes compared to the volume of the reaction solution (86.5 mL).

In the present Example 1, yield was improved while the chemical purity and the optical purity were maintained, compared to the Comparative Example 1.

Better yields than in Comparative Example 1 were obtained when water added was in the range of 0 to 0.98 volumes and isopropyl alcohol added was in the range of 0.14 to 0.56 volumes in step (2), relative to the volume of the reaction solution of step (1) in which the N-protected amino acid had been generated. Among the conditions tested, the highest yields were obtained when 0.49 to 0.75 volumes of water and 0.27 volumes of isopropyl alcohol were added (conditions F and G).

Moreover, in the method of the present invention, the extraction step and the concentration step were eliminated, and the number of organic solvents used was reduced from two (ethyl acetate and n-heptane) to one (isopropyl alcohol). Moreover, with respect to the relative volumes of solvents used from step (1) up to the obtainment of Cbz-L-CHG, while Comparative Example used about 1.7 volumes of organic solvents relative to the reaction volume of step (1) (that is, 2990 L of the reaction solution versus total 5130 L of ethyl acetate and n-heptane), the present Example used about 0.14 to 0.55 volumes of organic solvent (86.5 mL reaction volume versus 12.1 to 48.4 mL isopropyl alcohol), which represents a significant reduction in the amount of organic solvent used.

Industrial Applicability

According to the present invention, it is now possible to produce N-protected amino acids without extraction/concentration steps and with reduced usage of organic solvents during the production process.

What is claimed is:

1. A method for producing N-protected amino acid comprising:
    (1) a step of introducing a protecting group to an amino group of an amino acid under an alkaline condition and thus generating an N-protected amino acid,
    (2) a step of adding a water-soluble organic solvent, and optionally water, to the above reaction solution, and
    (3) a step of neutralizing or acidifying the reaction solution following step (2) and obtaining the N-protected amino acid in the crystal form.

2. The method according to claim 1, wherein the amino acid is L-cyclohexylglycine.

3. The method according to claim 1 or 2, wherein the N-protected amino acid is N-carbobenzyloxy-L-cyclohexylglycine.

4. The method according to claim 1, wherein the water-soluble organic solvent is isopropyl alcohol.

5. The method according to claim 1, wherein 0 to 0.98 volumes of water and 0.14 to 0.56 volumes of isopropyl alcohol are added in step (2) relative to the reaction volume of step (1) in which the N-protected amino acid has been generated.

6. The method according to claim 1, wherein 0.01 to 0.98 volumes of water and 0.14 to 0.56 volumes of isopropyl alcohol are added in step (2) relative to the reaction volume of step (1) in which the N-protected amino acid has been generated.

7. The method according to, claim 1 wherein 0.49 to 0.75 volumes of water and 0.27 volumes of isopropyl alcohol are added in step (2) relative to the reaction volume of step (1) in which the N-protected amino acid has been generated.

* * * * *